United States Patent
Akamatsu et al.

[11] Patent Number: 6,142,752
[45] Date of Patent: *Nov. 7, 2000

[54] CENTRIFUGAL FLUID PUMP ASSEMBLY

[75] Inventors: Teruaki Akamatsu, Kyoto; Toshihiko Nojiri, Kanagawa; Takayoshi Ozaki; Minoru Suzuki, both of Shizuoka, all of Japan

[73] Assignee: NTN Corporation, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/149,480

[22] Filed: Sep. 8, 1998

[30] Foreign Application Priority Data

Sep. 5, 1997 [JP] Japan ................................. 9-257891

[51] Int. Cl.$^7$ ........................................... F04B 17/00

[52] U.S. Cl. .......................... 417/420; 417/44.2; 417/63; 623/3

[58] Field of Search ................. 623/3; 606/151; 417/420, 44.2, 63

[56] References Cited

U.S. PATENT DOCUMENTS

| | | | |
|---|---|---|---|
| 4,964,847 | 10/1990 | Prince | 604/4 |
| 5,725,357 | 3/1998 | Nakazeki | 417/18 |
| 5,798,454 | 8/1998 | Nakazeki | 73/54.28 |

*Primary Examiner*—Charles G. Freay
*Assistant Examiner*—Ehud Gartenberg
*Attorney, Agent, or Firm*—Burns, Doane, Swecker & Mathis, L.L.P.

[57] ABSTRACT

A centrifugal fluid pump assembly has a pump body and a controller. The pump body has a housing, a pump section having an impeller rotating inside the housing, an impeller rotational torque generating section having a motor for rotating the impeller and an impeller position control section. The impeller rotates without contacting the housing. The controller has an impeller-floating position control function for changing the floating position of the impeller inside the housing by using the impeller position control section, a function of measuring electric current for driving the motor and a fluid viscosity calculation function for calculating a viscosity of fluid by utilizing a variation amount of the motor-driving electric current obtained by changing the floating position of the impeller.

17 Claims, 7 Drawing Sheets

CENTRIFUGAL FLUID PUMP ASSEMBLY

BACKGROUND OF THE INVENTION

The invention relates to a centrifugal fluid pump assembly for pumping a medical fluid, typically blood.

In modem medical treatment, centrifugal blood pumps are often used in artificial heart/lung units for extracorporeal blood circulation. Centrifugal pumps of the magnetic coupling type wherein a driving torque from an external motor is transmitted to the impeller through magnetic coupling are commonly used because the physical communication between the blood chamber of the pump and the exterior can be completely excluded to prevent invasion of bacteria.

In general, centrifugal blood pumps include a housing having a blood inlet port and a blood outlet port and an impeller accommodated for rotation in the housing for feeding blood by a centrifugal force developed during rotation. The impeller having magnetic pieces of permanent magnet disposed therein is rotated by a rotational torque generating mechanism which includes a rotor having magnets for attracting the magnetic pieces of the impeller and a motor for rotating the rotor.

FIG. 11 shows an example of an artificial heart/lung unit using the blood pump. An artificial heart/lung unit 100 comprises a blood pump 101, an artificial lung 102, and a pressure gauge 103 serving as a measuring means. When the blood pump 101 is of centrifugal type, it is necessary to provide the artificial heart/lung unit 100 with a flow meter 104. The measuring devices such as the pressure gauge 103 and the flow meter 104 are expensive. Further, it is necessary to provide the artificial heart/lung unit 100 with increased number of connection portions of the measuring devices, which increases the possibility of coagulation of blood.

When the blood pump is used for the artificial heart/lung unit, blood is gathered at intervals of certain period of time to examine the state of the blood by a device. In the examination, a hematocrit value and the viscosity of the blood are changed by the use of hemodilution agent. The viscosity of the blood also changes in dependence on the temperature of the blood. A change in the viscosity of the blood changes the flow velocity distribution of the blood flowing in a flow passage. The change in hematocrit value and the flow velocity distribution are factors of errors of various flow meters.

That is, as the flow meter for the artificial heart/lung unit, an electromagnetic flow meter and an ultrasonic Doppler flow meter are used. In the electromagnetic flow meter, the dielectric constant of fluid affects an output voltage greatly, and the hematocrit value changes the dielectric constant of fluid greatly. Thus, a change of the hematocrit value is the factor a cause of errors. In the ultrasonic Doppler flow meter, the change in a flow rate distribution is a main factor cause of errors. Because the viscosity of blood changes flow rate distribution, the viscosity of the blood affects measurement accuracy. It is possible to correct the values by verifying a flow meter for each hematocrit value and viscosity. Because the hematocrit value and the blood viscosity are measured by the batch which requires blood-gathering, it has been impossible to perform such a correction in real time.

When a blood pump is embedded in the human body, it is difficult to install a flow meter and a pressure gauge therein because the space for accommodating them is small.

It is an object of the invention to a centrifugal fluid pump assembly having a viscosity calculation function capable of calculating the viscosity uf fluid easily and reliably.

SUMMARY OF THE INVENTION

According to an aspect of the invention, there is provided a centrifugal fluid pump assembly comprising a housing having a blood inlet port and a blood outlet port, a centrifugal fluid pump section including an impeller having a magnetic material disposed therein and accommodated for rotation in the housing and without contacting the housing to feed a fluid by a centrifugal force developed during its rotation, an impeller rotational torque generating section including a rotor having a magnet for attracting thereto the magnetic material of the impeller and a motor for rotating the rotor and an impeller position control section having an electromagnet. The controller has an impeller-floating position control function for changing the floating position of the impeller inside the housing by using the impeller position control section, a function of measuring electric current for driving the motor and a fluid viscosity calculation function for calculating a viscosity of a fluid by utilizing a variation amount of the motor driving electric current obtained by changing the floating position of the impeller by using the impeller-floating position control function.

BRIEF DESCRIPTION OF THE DRAWINGS

The above and other objects, features and advantages of the invention will be better understood by reading the following description, taken in conjunction with the accompanying drawings.

DETAILED DESCRIPTION OF THE PREFERRED EMBODIMENTS

An embodiment of the centrifugal fluid pump assembly according to the invention applied to a blood pump is described with reference to the accompanying drawings.

Figure 1:
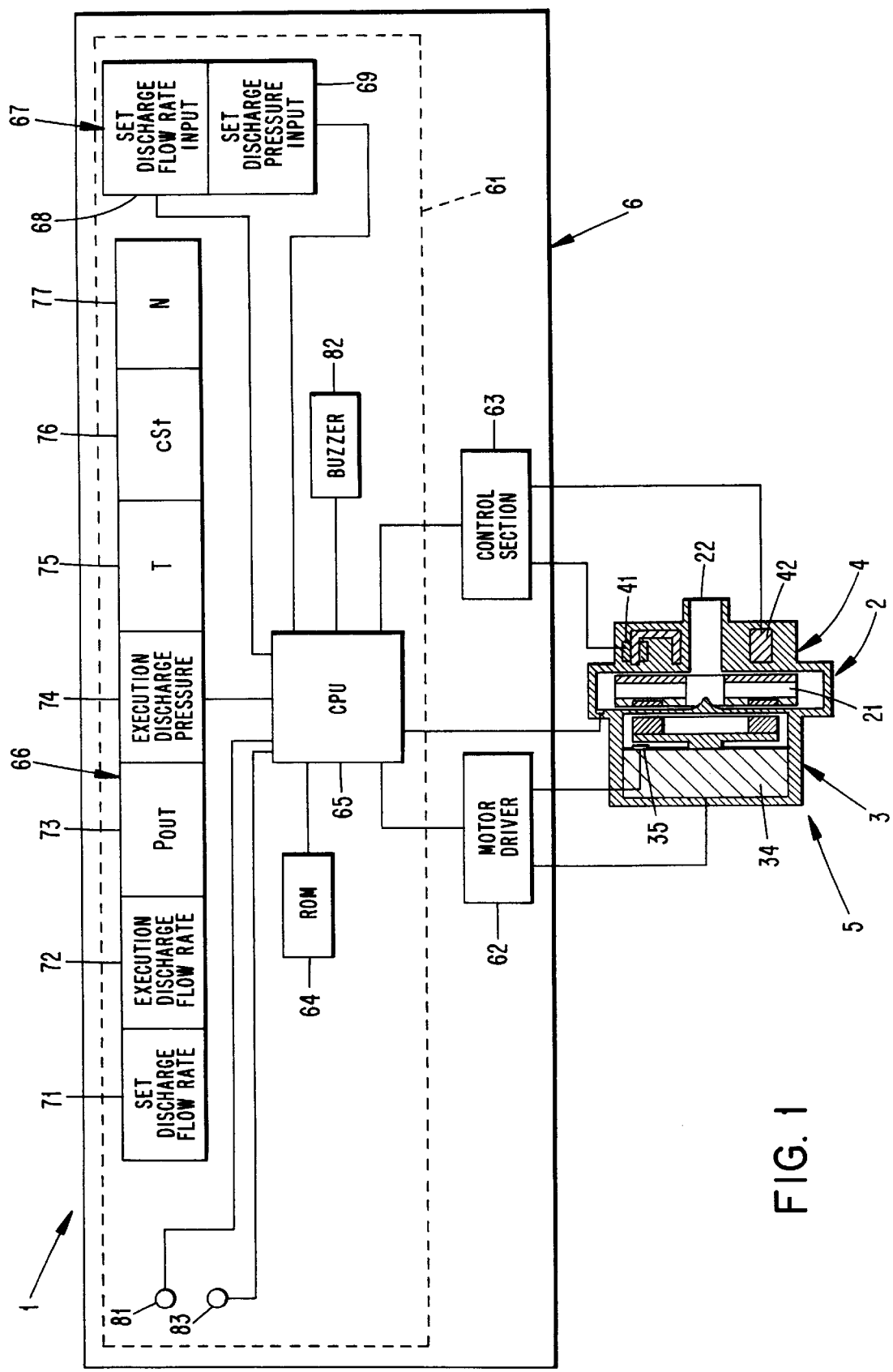
FIG. 1 is a block diagram showing a centrifugal fluid pump assembly according to an embodiment of the invention.
Figure 2:
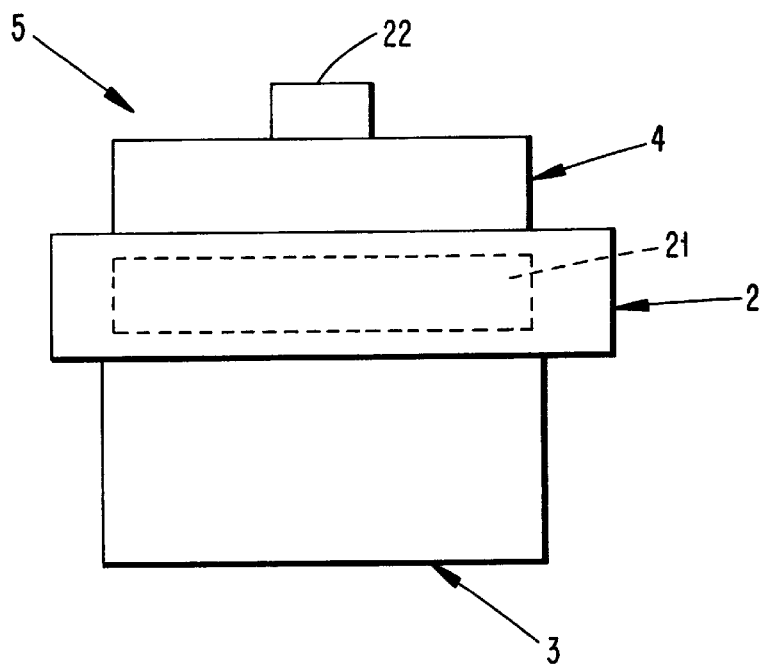
FIG. 2 is a front view showing an example of a pump body of the centrifugal fluid pump assembly of the invention.
Figure 3:
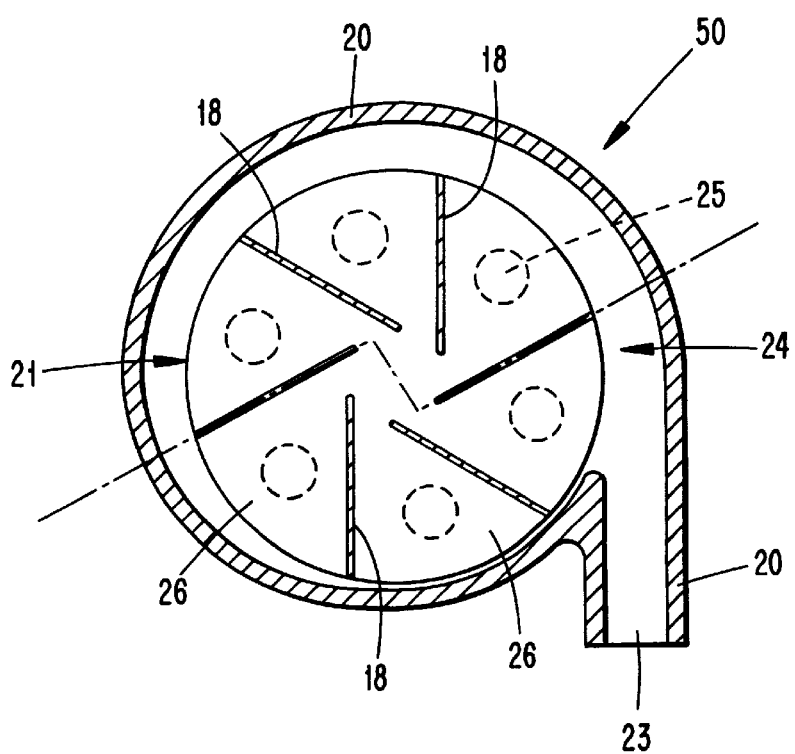
FIG. 3 is a horizontal cross-sectional view showing the pump assembly of the invention shown in FIG. 2 and obtained by cutting it horizontally at the position of an impeller.
Figure 4:
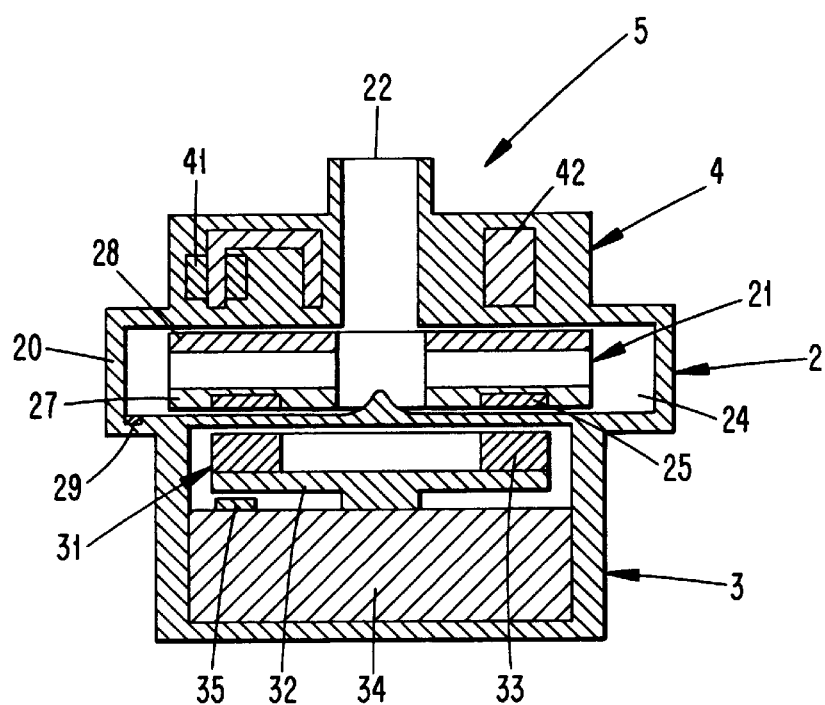
FIG. 4 is a vertical sectional view showing the pump assembly of an embodiment of the invention shown in FIG. 2.
Figure 5:
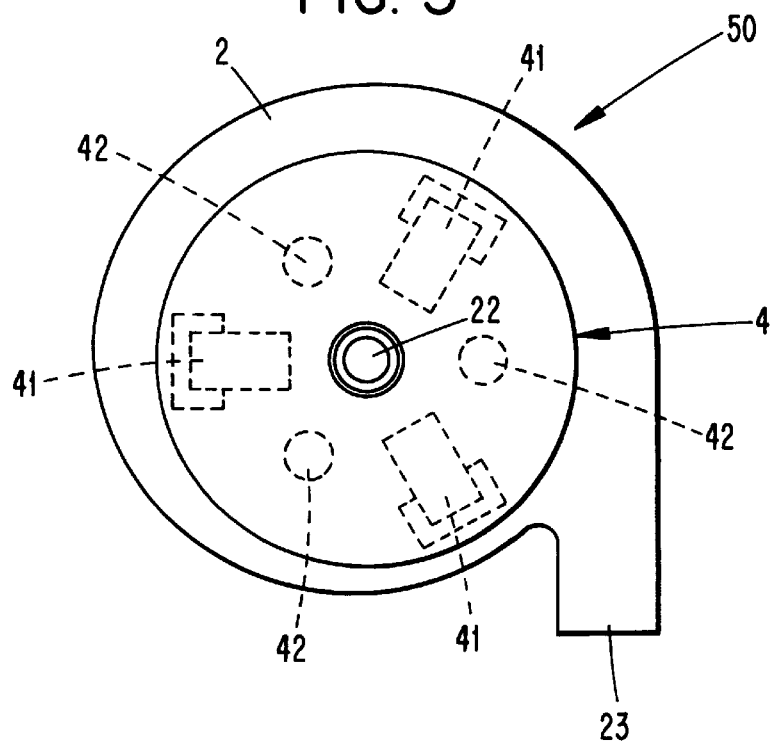
FIG. 5 is a plan view showing the pump body of the centrifugal fluid pump assembly of the invention shown in FIG. 2.

FIG. 1 is a block diagram showing a centrifugal fluid pump assembly according to an embodiment of the invention. FIG. 2 is a front view showing an example of the pump body of the centrifugal fluid pump assembly of the invention FIG. 3 is a horizontal cross-sectional view showing the pump assembly of the invention shown in FIG. 2 and obtained by cutting it horizontally at the position of an impeller. FIG. 4 is a vertical sectional view showing the pump assembly of an embodiment of the invention shown in FIG. 2. That is, FIG. 4 shows a state obtained, with the impeller cut along a curved dot-and-chain line in FIG. 3. FIG. 5 is a plan view showing the pump body of the centrifugal fluid pump assembly of the invention shown in FIG. 2.

A centrifugal fluid pump assembly 1 of the invention comprises a pump body 5 in which the impeller 21 rotates without contacting the housing 20 and a controller 6. The pump body 5 comprises a housing 20 having a blood inlet port 22 and a blood outlet port 23, a centrifugal fluid pump section 2 including an impeller 21 having a magnetic material 25 disposed therein and accommodated for rotation in the housing 20 and without contacting the housing 20 to feed a fluid by a centrifugal force developed during its rotation, an impeller rotational torque generating section 3 including a rotor 31 having a magnet 33 for attracting thereto the magnetic material 25 of the impeller 21 of the centrifugal fluid pump section 2 and a motor 34 for rotating the rotor 31, and an impeller position control section 4 having an electromagnet 41.

The controller 6 has or an impeller-floating position control function for changing the floating position of the impeller 21 inside the housing 20 by using the impeller position control section 4, a function of measuring electric current for driving the motor 34, and a fluid viscosity calculation function for calculating a viscosity of fluid by utilizing a variation in the amount of the motor-driving electric current obtained by changing the floating position of the impeller 21 by using the impeller-floating position control function.

Since the fluid pump assembly of the invention is typically applied as a blood pump, the following description refers to its embodiment as a blood pump.

As shown in FIGS. 2 to 5, the pump body 5 of the centrifugal fluid pump assembly comprises a housing 20 having the blood inlet port 22 and the blood outlet port 23, the centrifugal fluid pump section 2 including the impeller 21 rotating inside the housing 20 to feed blood by the centrifugal force generated during its rotation, the impeller rotation torque generating section 3 (uncontrolled magnetic bearing section) for the impeller 21, and the impeller position control section 4 (controlled magnetic bearing section) for the impeller 21.

The uncontrolled magnetic bearing section 3 and the controlled magnetic bearing section 4 cooperate such that the impeller 21 rotates while it is held in position within the housing 20.

The housing 20 has the blood inlet port 22 and the blood outlet port 23 and is formed of a non-magnetic material. The housing 20 defines therein the blood chamber 24 in fluid communication with the blood inlet and outlet ports 22 and 23. The impeller 21 is accommodated within the housing 20. The blood inlet port 22 protrudes from near the center of the upper surface of the housing 20 in a substantially vertical direction. The blood outlet port 23 projects from a side surface of the generally cylindrical housing 20 in a tangential direction.

The disc-shaped impeller 21 having a through-hole in the center thereof is accommodated within the blood chamber 24 of the housing 20. The impeller 21 includes a disc-shaped member or lower shroud 27 defining the lower surface thereof, an annular plate-shaped member or upper shroud 28 defining the upper surface thereof and opening at the center thereof, and a plurality of (six in the illustrated embodiment) vanes 18 (see FIG. 3) formed between the lower and upper shrouds 27 and 28.

The vanes 18 define a corresponding plurality of (six in the illustrated embodiment) blood passages 26 between two adjacent ones and between the lower and upper shrouds.

Each blood passage 26 extends from the center opening to the outer periphery of the impeller 21 in a curved fashion. Differently stated, the vanes 18 are formed between adjacent blood passages 26. In the illustrated embodiment, the vanes 18 and blood passages 26 are respectively provided at equiangular intervals and in substantially the same shape.

A plurality of (six in the illustrated embodiment) magnetic materials 25 are embedded in the impeller 21. The magnetic materials 25 are permanent magnets and serve as follower magnets.

The magnetic material 25 is embedded in the impeller 21. The magnetic material 25 is a permanent magnet and serves as a follower magnet. Pieces of magnetic material 25 are provided in order that the impeller 21 be attracted away from the blood inlet port 22 by a permanent magnet 33 in the rotor 31 of the rotational torque generating section 3 to be described later and that the rotational torque be transmitted from the torque generating section 3 to the impeller 21.

Preferably, pieces of the magnetic materials 25 are embedded in the impeller. Embedding a plurality of discrete magnetic pieces 25 in the impeller also ensures magnetic coupling with the rotor 31 to be described later. Each magnetic piece 25 is preferably circular in horizontal cross section.

The impeller 21 further includes a magnetic member 28 which itself constitutes an upper shroud or to which is attached to an upper shroud. In the illustrated embodiment, the upper shroud in its entirety is constructed of the magnetic member 28. The magnetic member 28 is provided in order that an electromagnet 41 of the impeller position control section 4 to be described later magnetically attracts the impeller 21 toward the blood inlet port 22. The magnetic member 28 may be formed of magnetic stainless steel, nickel or soft iron.

The impeller position control section 4 and the rotational torque generating section 3 constitute a non-contact type magnetic bearing, which magnetically attracts the impeller 21 from opposite directions to steadily hold the impeller 21 at a proper position out of contact with the inner surface of the housing 20 so that the impeller 21 may rotate within the housing 20 without contacting its inner surface.

Figure 8:
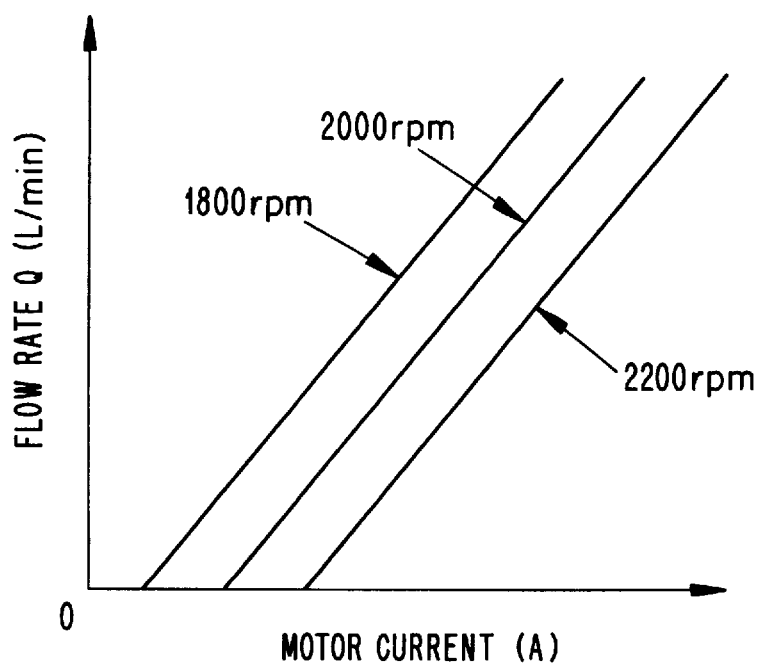
FIG. 8 is a view showing the relationship between a discharge flow rate of the centrifugal fluid pump assembly and the electric current for driving the motor.

Included in the rotational torque generating section 3 are the housing 20, the rotor 31 accommodated in the housing 20, and a motor for rotating the rotor 31 (whose internal structure is not shown in FIG. 8). The rotor 31 includes a rotating disc 32 and a plurality of permanent magnets 33 disposed on one surface (facing the fluid pump) of the rotating disc 32. The rotor 31 at its center is fixedly secured to the rotating shaft of the motor 34. The plurality of permanent magnets 33 are equiangularly distributed in accordance with the magnetic pieces 25 of the impeller 21, that is, the number and location of permanent magnets 33 are coincident with the number and location of magnetic pieces 25 (which are also permanent magnets).

Understandably, the impeller rotation torque generating section 3 is not limited to the illustrated one having the rotor and motor. For example, an arrangement of stator coils may be used as long as it can attract the magnetic pieces (of permanent magnets) 25 of the impeller 21 to drive the impeller for rotation.

The impeller rotation torque generating section 3 is provided with a sensor 35 for detecting the number of rotations of the motor 34 or that of the rotor 31. Optical or magnetic sensors can be used as the sensor 35. The number of rotations of the motor 34 or that of the rotor 31 may be detected by a counter electromotive force which is generated to the motor coils.

Included in the impeller position control section 4 are a plurality of electromagnets 41 accommodated in the housing 20 and attracting the magnetic member 28 of the impeller 21 thereto and a plurality of position sensors 42 for detecting the position of the magnetic member 28 of the impeller 21. In the impeller position control section 4, a plurality of (typically three) electromagnets 41 and a plurality of (typically three) sensors 42 are respectively arranged at equiangular intervals while the angle between one electromagnet 41 and an adjacent sensor 42 is also equal. The electromagnet 41 consists essentially of a core and a coil. Three electromagnets 41 are arranged in the embodiment. More than three electromagnets, for example, four electromagnets may be arranged. By adjusting the electromagnetic forces of the electromagnets 41 in accordance with the results of detection of the position sensors 42 to be described later, forces acting on the impeller in a center axis (z-axis) direction can be balanced and moments about x and y axes perpendicular to the center axis (z-axis) can be equal.

The position sensor 42 detects the distance of a gap between the electromagnet 41 and the magnetic member 28 and produces an output of detection which is fed back to a control section 63 for controlling electric current applied to the coil of the electromagnet 41. Even when a radial force as by gravity acts on the impeller 21, the impeller 21 is held at the center of the housing 20 by virtue of restoring forces of a magnetic flux between the permanent magnet 25 of the impeller 21 and the permanent magnet 33 of the rotor 31 and restoring forces of a magnetic flux between the electromagnet 41 and the magnetic member 28.

The controller 6 will be described below with reference to FIG. 1.

The controller 6 has an impeller position control function, an impeller rotation torque control function, the impeller-floating position control function for changing the impeller-floating position of the impeller 21 inside the housing 20 by using the impeller position control function, the electric current measuring function of measuring the electric current for driving the motor 34, and the fluid viscosity calculation function for calculating the viscosity of the fluid by utilizing a variation amount of the motor-driving electric current obtained by changing the floating position of the impeller 21 by means of the impeller-floating position control function.

More specifically, the controller 6 has a controller body 61, a motor driver 62, and the control section 63 for controlling the position of the impeller 21.

The motor driver 62 outputs a voltage, corresponding to the number of rotations (rotation speed) of the motor 34, transmitted (issued) thereto from the controller body 61 to rotate the motor 34.

The control section 63 controls electric current and/or a voltage which is applied to the electromagnet 41 so as to maintain the floating position of the impeller 21 outputted (issued) from the control section 63. Signals indicating the result obtained by the detection of the three position sensors 42 are transmitted to the control section 63. Upon receipt of the signals, the control section 63 controls electric current flowing through the three electromagnets 41 so that forces acting in the center axis (z-axis) direction of the impeller 21 are balanced with one another and moments about the x-axis and the y-axis perpendicular to the center axis (z-axis) can be equal to each other. It is possible to transmit the result detected by position sensors 42 to the controller body 61 so that the controller body 61 outputs voltages to the three electromagnets 41.

The controller body 61 comprises a storing section (ROM) 64, a CPU 65, a display section 66, and an input section 67. The display section 66 includes a portion 71 for displaying a set discharge flow rate, a portion 72 for displaying an execution discharge flow rate, a portion 73 for displaying a set discharge pressure, a portion 74 for displaying an execution discharge pressure, a portion 75 for displaying the temperature of fluid, a portion 76 for displaying the viscosity of fluid, and a portion 77 for displaying the number of rotations of the impeller 21. The input section 67 includes a portion 68 for inputting the set discharge flow rate thereto and a portion 69 for inputting the set discharge pressure thereto.

The controller body 61 has a data storing section 64 for storing relational data relating to fluid viscosity—a variation in the amount of motor-driving electric current obtained in advance by measuring the relationship between fluid viscosity and a variation in the amount of motor-driving electric current which is changed by a shift of an impeller-floating position or relational expression data (for example, data of a correlative equation or data of a viscosity calculation equation) determined from the relational data relating to fluid viscosity—a variation in the amount of motor-driving electric current. The fluid viscosity calculation function calculates the fluid viscosity by using the data (the relational data or the relational expression data) stored by the data storing section 64 and the variation in the amount of motor-driving electric current obtained by changing the floating position of the impeller 21 using the impeller-floating position control function.

In other words, the storing section 64 of the controller body 61 stores the relational data relating to fluid viscosity—a variation in the amount of motor-driving electric current obtained in advance by measuring the relationship between the fluid viscosity and the variation in the amount of the motor-driving electric current which is changed by a shift of the impeller-floating position or the data of the correlative equation (data of the viscosity calculation equation) determined from the -data relating to fluid viscosity—a variation in the amount of motor-driving electric current.

Figure 6:
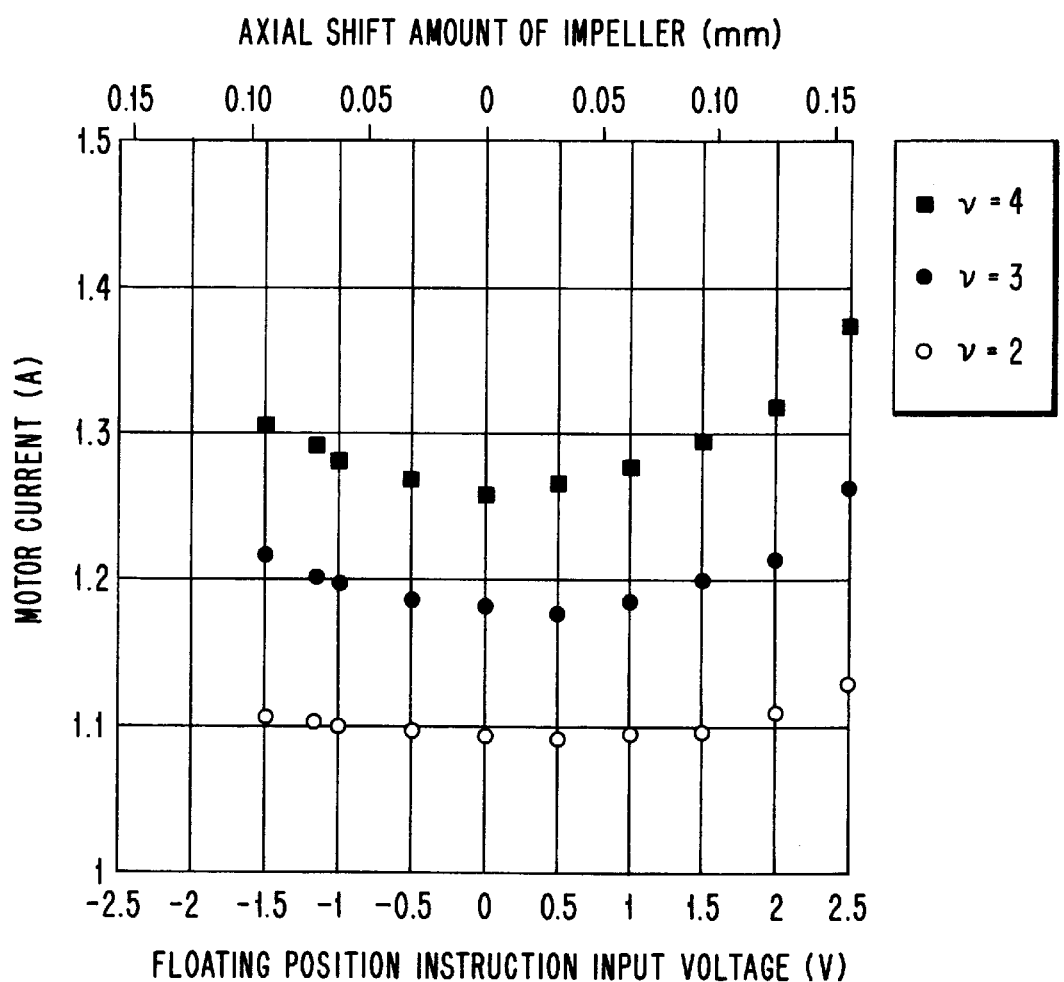
FIG. 6 is a view showing the relationship between a variation amount of an impeller-floating position and electric current for driving a motor of the centrifugal fluid pump assembly of the invention.

FIG. 6 shows the relationship between the variation amount of the floating position of the impeller 21 having a diameter of 50 mm and the motor-driving electric current in the case where the motor 34 (impeller) is rotating at a constant speed of 2000 rpm and the flow rate is 5 L/min when fluids (blood) having viscosities (cSt) 2, 3, and 4 are used. The numerals shown along the lowermost line of the abscissa are input voltages for instructing an impeller-floating position (hereinafter referred to as instruction input voltage). The controller body 61 adjusts electric current flowing through the electromagnet 41 via the control section 63 such that the impeller 21 is located at an impeller-floating position (input voltages shown along the uppermost line of the abscissa of FIGS. 6) corresponding to the instruction input voltage. In the embodiment, the reference numerals shown along the uppermost line of the abscissa of FIG. 6 are the variation in the impeller-floating position corresponding to the instruction input voltage. The instruction at (+) side in FIG. 6 indicates that the impeller 21 is shifted to the motor side (toward impeller rotation torque generating section 3), whereas the instruction at (−) side in FIG. 6 indicates that the impeller 21 is shifted to the electromagnet side (toward impeller position control section 4). More specifically, in the embodiment, the gap between the lower surface of the impeller 21 and the inner surface of the housing 20 at the side of the impeller rotation torque generating section 3 in the axial direction thereof is 0.25 mm when the value of an input voltage for changing the impeller-floating position (voltage change amount for position change) is 0 (normal state, namely, at a time when viscosity is not measured). When the impeller-floating position is shifted to the motor side by 0.15 mm, the gap between the lower surface of the impeller 21 and the inner surface of the housing 20 at the side of the impeller rotation torque generating section 3 in the axial direction of the impeller 21 is 0.1 mm.

A frictional force applied to the impeller 21 from the fluid changes according to the shift of the impeller-floating position. As a result, there is a change in impeller-rotating electric current applied to the motor. A variation in the amount of frictional torque or a variation in the amount of the motor-driving electric current is affected by the area of the upper and lower surfaces of the impeller 21, the gap between the impeller 21 and the inner surface of the housing 20 in the axial direction thereof, and the viscosity of the blood. As the blood viscosity becomes higher, the motor-driving electric current becomes increasingly high. Also, as the gap between the impeller 21 and the inner surface of the housing 20 in the axial direction thereof becomes smaller as a result of the approach of the impeller-floating position to the lower surface of at the motor side, the motor-driving electric current becomes increasingly high. The area of the upper and that of the lower surface of the impeller 21 are constant. Thus, the viscosity of the blood can be determined by utilizing the variation amount of the motor-driving driving electric current when the impeller-floating position is shifted.

The relationship between the gap between the impeller 21 and the inner surface of the housing 20 in the axial direction thereof and the variation in the amount of motor-driving electric current is changed not linearly but parabolically, as shown in FIG. 6. It is possible to obtain a sufficient amount of variation in electric current even in the case of fluid having a viscosity of about 2cSt by setting the amount of variation in the gap between the impeller 21 and the inner surface of the housing 20 in the axial direction thereof to 0.10 mm or more and preferably 0.15 mm or more. It is preferable to keep the gap therebetween at 0.05 mm or more to prevent the impeller 21 from contacting the inner surface of the housing 20.

Because the value of the motor-driving electric current depends on the flow rate of the fluid, it is difficult to calculate the viscosity of the fluid by using the motor-driving electric current value itself. But the variation amount in the motor-driving electric current value which is obtained by changing the impeller-floating position does not depend on the fluid flow rate. Thus, it is possible to calculate the fluid viscosity by using the variation in the amount of the motor-driving electric current. The variation of the impeller-floating position is so small as to be ignored, compared with the size of the pump. Thus, it is possible to ignore influence given by the variation of the impeller-floating position to the performance of the pump. More specifically, the flow rate hardly changes even when the impeller-floating position is shifted. A change of the value of the motor-driving electric current depends on only a change in frictional loss between the inner surface of the housing 20 and the upper and lower surfaces of the disc-shaped impeller 21. That is, the impeller-floating position depends on the instruction input voltage and not on the fluid viscosity or the number of rotations of the motor 34.

Figure 7:
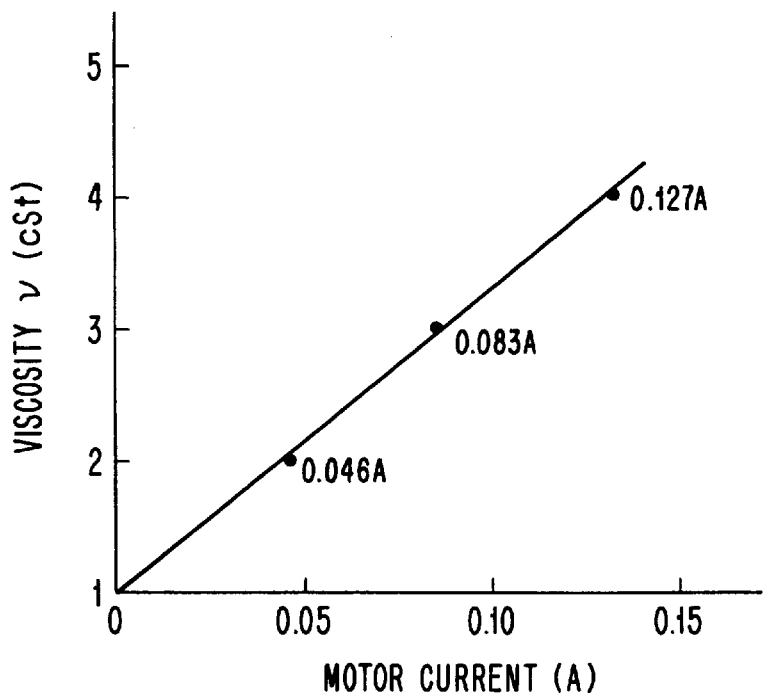
FIG. 7 is a view showing the relationship between a variation amount of the electric current for driving the motor of the centrifugal fluid pump assembly of the invention and fluid viscosity.

FIG. 7 shows the relationship between the fluid viscosity (blood viscosity) and the variation amount of the motor-driving electric current value obtained by subtracting (dividing) the motor-driving electric current value when the instruction input voltage for the impeller-floating position is 0 (variation of the impeller-floating position is 0 mm, the gap between the lower surface of the impeller 21 and the inner surface of the housing 20 at the side of the impeller rotation near the torque generating section 3 in the axial direction thereof is 0.25 mm) from the motor-driving electric current value when the variation in the amount (increased amount of voltage) of the instruction input voltage is 2.5V (variation amount of impeller-floating position is 0.15 mm, the gap between the lower surface of the impeller 21 and the inner surface of the housing 20 at the side of the impeller near the rotational torque generating section 3 in the axial direction thereof is 0.10 mm) shown in FIG. 6. FIG. 7 indicates that the fluid viscosity (blood viscosity) increases linearly with the variation in the amount of the motor-driving electric current. Further, from the relational data of fluid viscosity—variation in the amount of the motor-driving electric current, an equation which is a correlative equation (regression line) and also a viscosity calculation equation can be obtained. That is, in the pump of the embodiment, the viscosity calculation equation is expressed as follows:

Viscosity (v, cSt)=24.63×variation amount of motor-driving electric current (A)+0.90

In the embodiment, the ROM 64 stores the viscosity calculation equation.

The ROM 64 may store only the relational data of fluid viscosity—variation in the amount of the motor-driving electric current (raw data), and the CPU 65 may calculate the correlative equation (viscosity calculation equation) before calculating the viscosity. In this case, the controller 6 has the function of calculating the correlative equation and the viscosity calculation equation.

In order to calculate the viscosity by using the viscosity calculation equation, the variation amount of the motor-driving electric current or the motor-driving electric current value is inputted to the CPU 65.

A signal relating to the number of rotations of the motor 34 detected by the sensor 35, of the impeller rotation torque generating section 3, for detecting the number of rotations of the motor 34 or detected by a counter electromotive force waveform is inputted to the controller body 61 (namely, motor driver 62). The motor driver 62 converts the signal into a signal indicating the number of rotations of the motor 34. The signal indicating the number of rotations of the motor 34 is transmitted to the CPU 65. The instruction of the impeller-floating position may be outputted from the CPU 65 stepwise or ramp linearly or ramp nonlinearly.

The controller 6 may have a data-storing section 64 for storing relational data relating to fluid viscosity—variation in the amount of motor-driving electric current obtained in advance by examining, for each of a plurality (at least two) of rotations of the motor 34, the relationship between a fluid viscosity and a variation in the amount of motor-driving electric current which is changed by the shift of an impeller-floating position or relational expression data (for a example, data of viscosity calculation equation) determined from the relational data relating to fluid viscosity—variation amount of motor-driving electric current. This construction allows a change of the number of rotations of the motor 34 to be close to one of rotations of the pump stored in the data-storing section 64, thus eliminating the need for changing the number of rotations of the motor 34 greatly in measuring the blood viscosity. Further, it is possible to calculate the blood viscosity for each of a plurality of the number of rotations of the motor 34 and determine an average value of the blood viscosity.

The controller body 61 outputs an alarm signal when the blood viscosity determined by the blood viscosity calculation function becomes less than a first set value. More specifically, the controller body 61 has a lamp 81 and a buzzer 82 for giving an alarm when the blood viscosity is reduced. More specifically, when the blood viscosity is less than the first set value, the CPU issues an instruction of flashing the alarm lamp 81 and sounding the buzzer 82.

The controller body 61 outputs an alarm signal when the blood viscosity determined by the blood viscosity calculation function becomes more than a second set value. More specifically, the controller body 61 has a lamp 83 for giving an alarm when the blood viscosity increases. More specifically, when the blood viscosity becomes more than the second set value, the CPU issues an instruction of flashing the alarm lamp 83 and sounding the buzzer 82. The buzzer 82 is commonly used when the blood viscosity is less than the first and second set values. The buzzer 82 can give a single alarm sound or a plurality of alarm sounds can be used. In order to distinguish the reduction of the viscosity and the increase thereof, it is preferable that the buzzer 82 gives a different alarm sound depending on each state of the blood viscosity.

When a blood viscosity becomes high a thrombus is likely to be formed. Bleeding may cause the blood viscosity to drop. An alarm signal outputted from the controller body 61 when a measured viscosity is too high or too low compared with the permissible viscosity allows, doctors or patients to give or receive medical treatment quickly.

The controller body 61 stores relational data relating to a discharge flow rate obtained by in advance examining the relationship among the motor-driving electric current, the number of rotations of the motor 34, and the discharge flow rate or relational expression data obtained by calculating the above relational data. The controller body 61 has a discharge flow rate calculation function of calculating the discharge flow rate by using an actual value of motor-driving electric current, the number of rotations of the motor 34, and the relational data. In particular, the controller body 61 has the discharge flow rate calculation function of calculating the discharge flow rate by using the actual value of the motor-driving electric current, the actual number of rotations of the motor 34, the relational expression data, and a fluid viscosity determined by the above-described fluid viscosity calculation function.

FIG. 8 shows the relationship between the discharge flow rate of a magnetic floating type centrifugal pump and the motor-driving electric current examined by changing the number of rotations of the motor 34. The characteristic of the magnetic floating type centrifugal pump shown in FIG. 8 changes depending on the gap between the housing 20 and the impeller 21 in the axial direction thereof shown in FIG. 4 and the fluid viscosity. But it is possible to obtain the discharge flow rate from the motor-driving electric current and the number of rotations of the motor 34 by verifying them for each pump in advance, as shown in FIG. 8.

As described above, in order to obtain the discharge flow rate without measuring it, the controller body 61 stores the relational data relating to the discharge flow rate obtained by in advance examining the relationship among the motor-driving electric current, the number of rotations of the motor 34, and the discharge flow rate or relational expression data obtained by calculating the relational data. The discharge flow rate is calculated by using the actual motor-driving electric current, the number of rotations of the motor 34, and the relational expression data.

More specifically, when constant electric current and voltage are supplied to the motor 34 by the function of controlling the number of rotations of the motor 34 to rotate the impeller 21 at a constant speed of 2200 rpm, the flow rate can be determined from the number of rotations of the motor 34 and the motor-driving electric current, as shown in FIG. 8 indicating the characteristic of the magnetic floating type centrifugal pump. In this case, based on an instruction issued by the CPU 65 of the controller 6, the motor driver 62 drives the motor 34 such that the number of rotations of the motor 34 is 2200 rpm.

Figure 9:
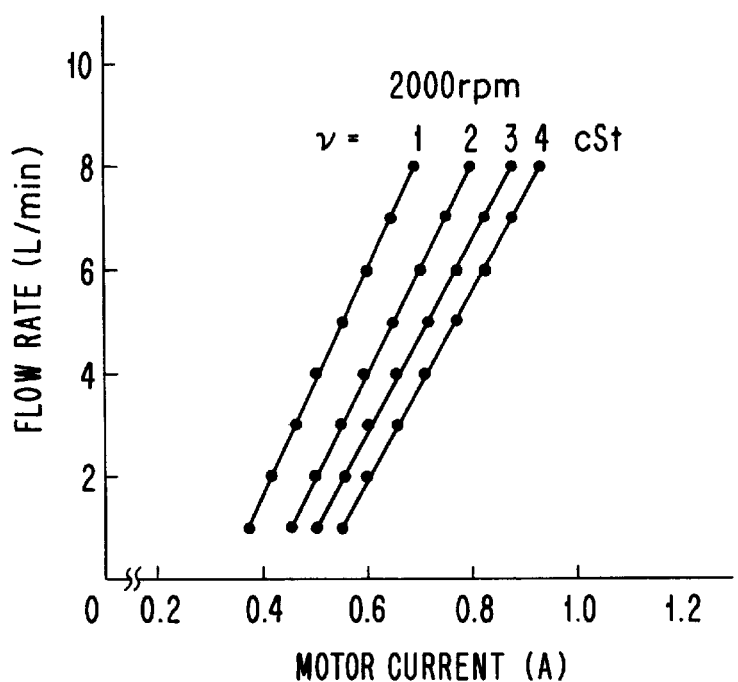
FIG. 9 is a view showing the characteristic of the centrifugal fluid pump assembly obtained by examining the relationship between the electric current for driving the motor and a flow rate set at a constant motor rotation speed when the number of rotations of the motor is changed.

However, as shown in FIG. 9 the characteristic of the magnetic floating type centrifugal pump obtained when the relationship between the motor-driving electric current and the flow rate at a constant motor rotation speed is examined by changing the blood viscosity, values of electric current by which a constant flow rate is obtained are different from each other depending on blood viscosities v=1, 2, 3, and 4 even though the motor rotates at a constant speed of 2000 rpm in calculating the flow rate from the motor-driving electric current and the number of rotations of the motor 34. Thus, the variation in the amount of blood viscosity causes an error.

In order to solve the problem, the controller body 61 has the discharge flow rate calculation function for calculating the discharge flow rate by using the actual value of motor-driving electric current, the number of rotations of the motor 34, the relational expression data, and the fluid viscosity obtained by the calculation performed by the fluid viscosity calculation function, thus making a viscosity correction and determining a correct execution discharge flow rate.

The CPU 65 issues an instruction to the display section to display the number of rotations of the motor 34 and also to the a portion 72 for displaying an execution discharge flow rate to display a discharge flow rate obtained by a calculation including the correction of the blood viscosity.

According to the pump assembly 1 of the invention, in order to feed the fluid based on a set flow rate, the controller body 61 has a function of inputting the set flow rate and storing the set flow rate and a discharge flow rate control function of controlling the discharge flow rate so that the discharge flow rate approaches the set flow rate by comparing the discharge flow rate obtained by the calculation performed by the discharge flow rate calculation function and the set flow rate with each other and controlling the number of rotations of the motor 34 by using the result obtained by the comparison.

Feedback control can be used to execute the control of the discharge flow rate. In the feedback control, when the execution discharge flow rate (calculated value) is smaller than the set discharge flow rate, the number of rotations of the motor 34 is increased. When the execution discharge flow rate (calculated value) is greater than the set discharge flow rate, the number of rotations of the motor 34 is decreased. The controller body 61 has the function of comparing the discharge flow rate obtained by the calculation performed by the discharge flow rate calculation function and the set flow rate with each other and calculating the number of rotations of the motor 34 corresponding to the difference therebetween. The controller body 61 controls the discharge flow rate by adding the number of rotations of the motor 34 obtained by the function of calculating the number of rotations of the motor 34 corresponding to the difference therebetween to the number of rotations of the motor 34 currently instructed or subtracting the number of rotations of the motor 34 obtained thereby from the number-of rotations of the motor 34 currently instructed.

The controller body 61 has also a discharge pressure calculation function. That is, the controller body 61 has the discharge pressure calculation function of calculating the discharge pressure by directly or indirectly utilizing the fluid viscosity obtained by the calculation performed by the fluid viscosity calculation function. More specifically, the ROM 64 of the controller body 61 stores the relational data relating to the discharge pressure obtained by in advance examining the relationship among the motor-driving electric current, the number of rotations of the motor 34, and the discharge pressure or the relational expression data obtained by calculating the above relational data. The controller body 61 calculates the discharge pressure by using the calculated discharge flow rate (including correction of viscosity), the actual number of rotations of the motor 34 and the data (the relational data or the relational expression data ), thus giving an issue to the portion 72 for displaying an execution discharge flow rate to display the obtained discharge pressure.

Figure 10:
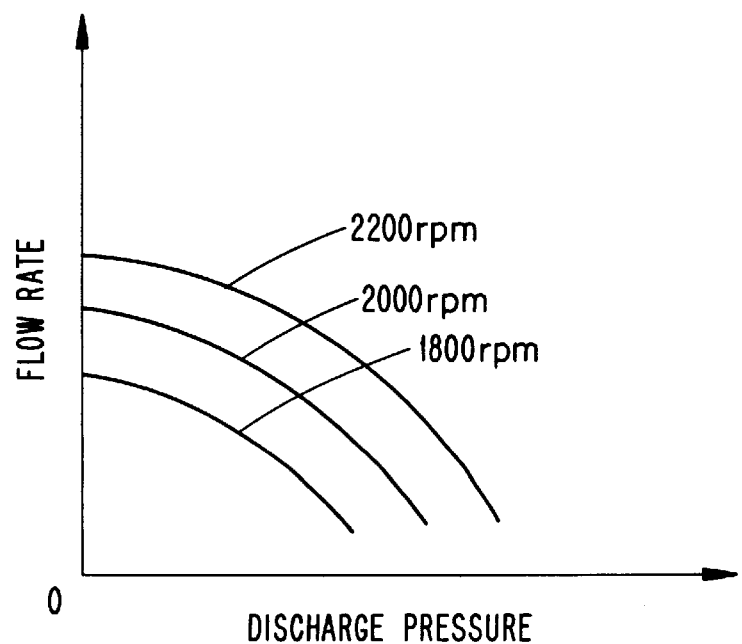
FIG. 10 is a view showing the characteristic of pump discharge flow rate discharge pressure at each rotation speed of the motor.
Figure 11:
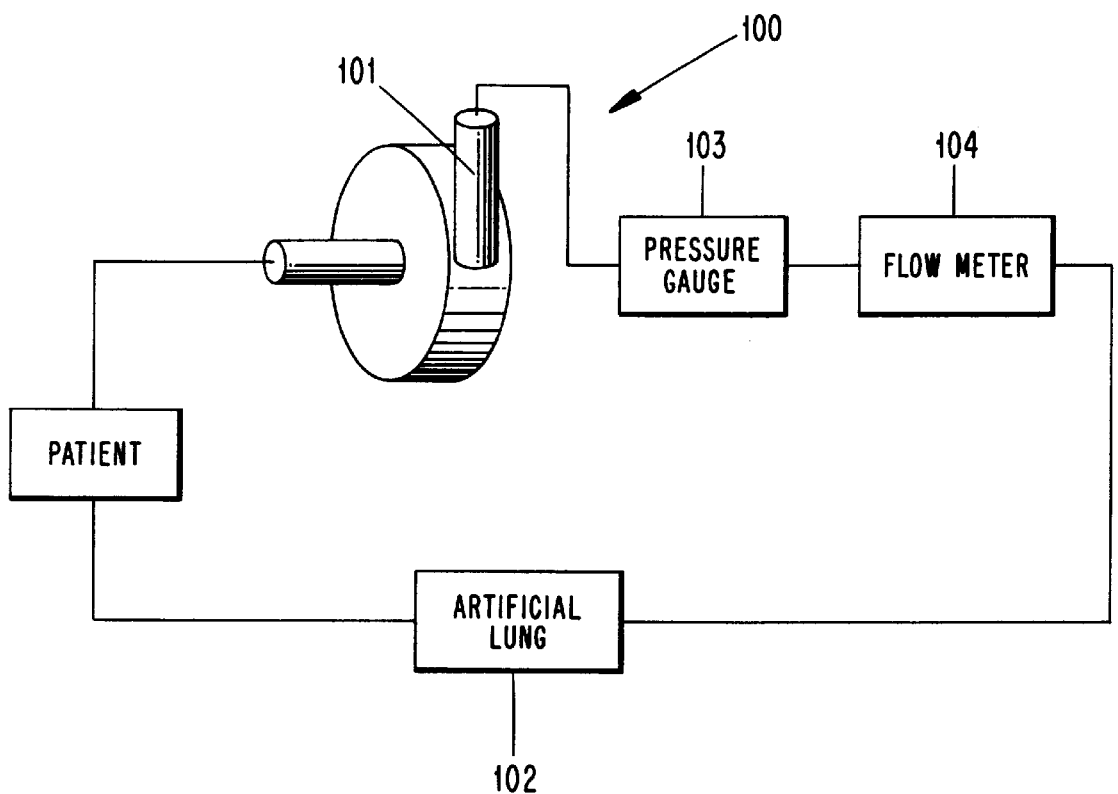
FIG. 11 is a view showing a conventional artificial heart/lung unit to which a blood pump is applied.

FIG. 10 shows the characteristic of pump discharge flow rate—discharge pressure at each rotation speed (number of rotations) of the motor 34. The characteristic of the magnetic floating type centrifugal pump shown in FIG. 10 changes, depending on a fluid viscosity. But as shown in FIG. 9, the discharge flow rate can be obtained from the motor-driving electric current and the number of rotations of the motor 34. The discharge pressure can be determined from the discharge flow rate and the number of rotations of the motor 34 as shown in FIG. 10.

As described above, the viscosity-corrected execution discharge flow rate can be calculated by the discharge flow rate calculation function. An execution discharge pressure can be calculated by using the execution discharge flow rate and the relational data relating to the discharge pressure obtained by in advance examining the relationship among the motor-driving electric current, the number of rotations of the motor 34, and the discharge flow rate stored by the controller body 61 or the relational expression data obtained by calculating the above relational data. Therefore, it is possible to obtain a correct viscosity-corrected execution discharge pressure without measuring it.

According to the pump assembly 1 of the invention, in order to feed the fluid based on a set pressure, the controller body 61 has a function of inputting the set discharge pressure and storing the set discharge pressure. Further, the controller body 61 compares the discharge pressure obtained by the calculation performed by the discharge pressure calculation function and the set discharge pressure with each other, and controls the number of rotations of the motor 34 by using the result obtained by the comparison. That is, the controller body 61 has a discharge pressure control function of controlling the discharge pressure so that the discharge pressure approaches the set discharge pressure.

Feedback control can be used to execute the control of the discharge pressure. In the feedback control, when the execution discharge pressure (calculated value) is smaller than the set discharge pressure, the number of rotations of the motor 34 is increased. When the execution discharge pressure (calculated value) is greater than the set discharge pressure, the number of rotations of the motor 34 is decreased. The controller body 61 has the function of comparing the discharge pressure obtained by the calculation performed by the discharge pressure calculation function and the set discharge pressure with each other and calculating the number of rotations of the motor 34 corresponding to the difference therebetween. The controller body 61 controls the discharge pressure by adding the number of rotations of the motor 34 obtained by the function of calculating the number of rotations of the motor 34 corresponding to the difference therebetween to the number of rotations of the motor 34 currently instructed or subtracting the number of rotations of the motor 34 obtained thereby from the number of rotations of the motor 34 currently instructed.

According to the centrifugal fluid pump assembly 1 of the invention, the pump section 2 has a blood temperature detector 29 (temperature sensor). The controller body 61 has a hematcrit value calculation function of calculating a hematcrit value by using a blood temperature detected by the blood temperature detector 29 and a blood viscosity calculated by the blood viscosity calculation function. Table 1 shows the result obtained by measuring the relationship among the viscosity of human blood, the hematcrit value, and blood temperature by using a rotary conic viscometer, thus indicating that it is possible to estimate the hematcrit value from the blood temperature and the blood viscosity.

TABLE 1

|  | Hematcrit value (%) | | | |
| --- | --- | --- | --- | --- |
| Blood temperature (° C.) | 20 | 30 | 40 | 50 |
| 20 | 4.0 | 5.2 | 7.8 | 9.1 |
| 30 | 2.9 | 3.8 | 4.6 | 5.8 |
| 37 | 2.0 | 3.1 | 3.9 | 4.8 |

Viscosity unit cSt

The viscosity calculation step of the centrifugal fluid pump assembly 1 of the invention will be described below briefly.

First, the CPU 65 stores a set flow rate or a set discharge pressure inputted to the controller body 61 from each input portion thereof before extracorporeal blood circulation is started. Then, the CPU 65 calculates a number of rotations of the motor 34 and a motor-driving electric current both corresponding to the set value, thus outputting the calculated value to the motor driver 62 to rotate the pump based on the condition. The CPU 65 outputs a voltage (instruction voltage for impeller-floating position) corresponding to a voltage of the electromagnet 41 of the impeller position control section 4 through the impeller position control section 3 so that the impeller-floating position is at the normal position (viscosity-uncounted time), namely, the gap between the lower surface of the impeller 21 and the inner surface of the housing 20 at the impeller rotation torque generating section-positioned side is 0.25 mm. In this manner, the feeding of the fluid starts. After circulation of the fluid starts, the CPU 65 alters the number of rotations of the motor 34 to the number of rotations of the motor 34 stored by the storing section and alters the instruction voltage for the impeller-floating position to change the impeller-floating position. For example, the instruction voltage for the impeller-floating position is altered to 2.5V. As a result, the impeller 21 moves by about 0.15 mm and the gap between the lower surface of the impeller 21 and the inner surface of the housing 20 at the impeller rotation torque generating section-positioned side is about 0.1 mm.

Values of the motor-driving electric current are sequentially inputted to the controller body 61 (CPU 65). The CPU 65 calculates a variation amount of the value of the motor-driving electric current from a motor-driving electric current value before altering the impeller-floating position and a motor-driving electric current value after altering the impeller-floating position. Then, to return the impeller-floating position to the normal position, the CPU 65 gives an instruction to alter the instruction voltage for the impeller-floating position. For example, when the instruction voltage for the impeller-floating position is set to 0V, the impeller 21 moves by about 0.15 mm, and the gap between the lower surface of the impeller 21 and the inner surface of the housing 20 at the impeller rotation torque generating section-positioned side is returned to about 0.25 mm.

The CPU 65 calculates the viscosity by using the variation amount of the motor-driving electric current value and the viscosity calculation equation stored by the ROM 64.

In conventional flow meters and pressure gauges, error occurs due to a viscosity change. However, the viscosity determined as described above can be utilized for correction of flow rates and pressures. Thus, it is possible to obtain discharge flow rates and discharge pressures with high accuracy.

The centrifugal fluid pump assembly of the invention comprises a housing having a blood inlet port and a blood outlet port, a centrifugal fluid pump section including an impeller having a magnetic material disposed therein and accommodated for rotation in the housing and without contacting the housing to feed a fluid by a centrifugal force developed during its rotation, an impeller rotational torque generating section including a rotor having a magnet for attracting thereto the magnetic material of the impeller and a motor for rotating the rotor and an impeller position control section having an electromagnet. The controller comprises an impeller-floating position control function for changing the floating position of the impeller inside the housing by using the impeller position control section, a function of measuring electric current for driving the motor, and a fluid viscosity calculation function for calculating a viscosity of fluid by utilizing a variation amount of the motor-driving electric current obtained by changing the floating position of the impeller by using the impeller-floating position control function.

According to the above construction, a fluid viscosity can be measured at real time and with ease by changing the floating position of the impeller without providing a specific device. Further, the measured viscosity can be used for management of fluid viscosity, for example, in giving an alarm indicating that the viscosity is abnormal, and for correction in determining a discharge flow rate and a discharge pressure by calculation without using a flow meter or a pressure gauge.

The controller stores relational data relating to a discharge flow rate obtained by in advance examining the relationship among the motor-driving electric current, the number of rotations of the motor, and the discharge flow rate or relational expression data obtained by calculating the above relational data. The controller has the discharge flow rate calculation function of calculating the discharge flow rate by using a fluid viscosity determined from the actual motor-driving electric current, the number of rotations of the motor, the relational expression data, and the above-described fluid viscosity calculation function. Therefore, by performing calculations and without using a flow meter, it is possible to determine a correct flow rate, namely, having few errors even though measured viscosities are different.

The controller has a function of inputting the set flow rate and storing the set flow rate, and a discharge flow rate control function of controlling a discharge flow rate so that the discharge flow rate approaches the set flow rate by comparing a discharge flow rate obtained by the calculation performed by the discharge flow rate calculation function and a set flow rate with each other, and controlling the number of rotations of the motor 34 by using the result obtained by the comparison. Thus, management of the discharge flow rate can be accomplished easily.

The controller has a discharge pressure calculation function of calculating a discharge pressure by using a calculated discharge flow rate obtained by the discharge pressure calculation function, the relational data relating to the discharge pressure obtained by in advance examining the relationship among the motor-driving electric current, the number of rotations of the motor, and the discharge pressure or the relational expression data obtained by calculating the above relational data, and the number of rotations of the motor. Therefore, by performing calculations and without using a flow meter, it is possible to determine a correct flow rate, namely, having few errors even though measured viscosities are different.

The controller has a function of inputting the set discharge pressure and storing the set discharge pressure, and has a discharge pressure control function of controlling the discharge pressure so that the discharge pressure approaches the set discharge pressure by comparing the discharge pressure obtained by the calculation performed by the discharge pressure calculation function and the set discharge pressure with each other, and controlling the number of rotations of the motor by using the result obtained by the comparison. Thus, management of the discharge flow rate can be accomplished easily.

While the present invention has been described with reference to preferred embodiments thereof, it is to be understood that the invention is not limited to the disclosed embodiments or constructions. On the contrary, the invention is intended to cover various modifications and equivalent arrangements included within the spirit and scope of the appended claims.

What is claimed is:

1. A centrifugal fluid pump assembly comprising a housing having a blood inlet port and a blood outlet port;

centrifugal fluid pump section including an impeller having a magnetic material disposed therein, the impeller being rotatable within the housing without contacting the housing for feeding a fluid by a centrifugal force developed during rotation of the impeller;

an impeller rotational torque generating section including a rotor and a motor for rotating the rotor, the rotor having a magnet for attracting thereto the magnetic material of the impeller;

an impeller position control section having an electromagnet;

a controller for changing the floating position of the impeller inside the housing using the impeller position control section, for measuring electric current for driving the motor, and for calculating a fluid viscosity based upon a variation in an amount of the motor-driving electric current obtained by changing the floating position of the impeller; and wherein the controller stores relational data relating to a discharge flow rate and calculates a discharge flow rate using an actual value of the motor-driving electric current, an actual number of rotations of the motor, the fluid viscosity calculated by the controller, and the relational data or a relational expression data.

2. The centrifugal fluid pump assembly according to claim 1, wherein the controller has a data storing section for storing relational data relating to fluid viscosity including variations in an amount of motor-driving electric current obtained in advance by examining the relationship between a fluid viscosity and a variation in an amount of motor-driving electric current which is changed by a shift of an impeller-floating position, or relational expression data determined from the relational data relating to fluid viscosity, and wherein the fluid viscosity is calculated using data stored by the data storing section and a variation in an amount of the motor-driving electric current obtained by changing the floating position of the impeller.

3. The centrifugal fluid pump assembly according to claim 1, wherein said controller has a data-storing section for storing relational data relating to fluid viscosity including a variation in an amount of motor-driving electric current obtained in advance by examining for each of a plurality of rotations of the motor, the relationship between a fluid viscosity and a variation in an amount of motor-driving electric current which is changed by a shift of an impeller-floating position, or relational expression data determined from the relational data relating to fluid viscosity, and wherein the fluid viscosity is calculated using the data stored by the data-storing section, the number of rotations of the motor, and a variation in an amount of the motor-driving electric current obtained by changing a floating position of the impeller.

4. The centrifugal fluid pump assembly according to claim 1, further comprising:

a magnetic member in the impeller, a plurality of fixed electromagnets for attracting the magnetic member of the impeller, the fixed electromagnets being located in the impeller position control section, and a position sensor for detecting a position the magnetic member of the impeller.

5. The centrifugal fluid pump assembly according to claim 1, wherein the centrifugal fluid pump assembly is a centrifugal blood pump assembly.

6. The centrifugal fluid pump assembly according to claim 2, wherein the centrifugal fluid pump assembly is a centrifugal blood pump assembly.

7. The centrifugal fluid pump assembly according to claim 5, further comprising:

a blood temperature detector, and wherein the controller calculates a hematocrit value using a blood temperature detected by the blood temperature detector and a calculated blood viscosity.

8. The centrifugal fluid pump assembly according to claim 6, further comprising:

a blood temperature detector, and wherein the controller calculates a hematocrit value using a blood temperature detected by the blood temperature detector and a calculated blood viscosity.

9. The centrifugal fluid pump assembly according to claim 5, wherein the controller outputs an alarm signal when a blood viscosity calculated by the fluid viscosity calculation function is less than a first set value.

10. The centrifugal fluid pump assembly according to claim 5, wherein the controller outputs an alarm signal when a blood viscosity calculated by the fluid viscosity calculation function is more than a second set value.

11. The centrifugal fluid pump assembly according to claim 1, wherein the controller inputs a set flow rate, stores the set flow rate, and controls a discharge flow rate so that the discharge flow rate approaches the set flow rate by comparing a calculated discharge flow rate to the set flow rate and controlling the number of rotations of the motor by using a result obtained by the comparison.

12. The centrifugal fluid pump assembly according to claim 1, wherein the controller calculates a discharge pressure by using a calculated discharge flow rate calculated by the controller, relational data relating to the discharge pressure obtained by advanced examination of the relationship between a motor-driving electric current, the number of rotations of the motor, and the discharge pressure or relational expression data obtained by calculating the above relational data.

13. The centrifugal fluid pump assembly according to claim 12, wherein the controller inputs a set discharge pressure stores the set discharge pressure, and controls a discharge pressure so that the discharge pressure approaches the set discharge pressure by comparing the calculated discharge pressure and the set discharge pressure and controlling the number of rotations of the motor by using a result obtained by the comparison.

14. The centrifugal fluid pump assembly according to claim 11, wherein the controller controls the number of rotations of the motor to control the discharge flow rate.

15. The centrifugal fluid pump assembly according to claim 13, wherein the controller controls the number of rotations of the motor to control the discharge pressure.

16. The centrifugal pump assembly according to claim 1 wherein the controller measures a first motor diving electric current associated with a first impeller-floating position and a second motor driving electric current associated with a second impeller-floating position and wherein the controller calculates the viscosity of the fluid based on a comparison of the first motor-driving electric current and second motor-driving electric current.

17. The centrifugal fluid pump assembly according to claim 1, wherein the controller stores relational data relating to a discharge flow rate obtained by an examination of the relationship between a motor-driving electric current, the number of rotations of the motor, and the discharge flow rate or the relational expression data obtained by calculating the relational data.

* * * * *

UNITED STATES PATENT AND TRADEMARK OFFICE
CERTIFICATE OF CORRECTION

PATENT NO. : 6,142,752
DATED : November 7, 2000
INVENTOR(S) : T. Akamatsu, et al.

Page 1 of 1

It is certified that error appears in the above-identified patent and that said Letters Patent is hereby corrected as shown below:

Column 1,
Line 7, "modem" is changed to -- modern --.
Lines 51 and 52, "the factor" is deleted.

Column 3,
Line 36, "or" is deleted.

Column 6,
Line 37, -- , -- is inserted between "position" and "or".
Line 56, "-data" is deleted, and -- data -- is inserted.

Column 7,
Line 32, "of" is changed to -- a --.

Column 8,
Line 22, "rotation" is deleted.
Line 26, after "variation" -- in the -- is inserted.

Column 9,
Line 6, "a" is deleted.
Line 7, after "of" -- a -- is inserted.

Signed and Sealed this

Second Day of October, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO. : 6,142,752
DATED : November 7, 2000
INVENTOR(S) : T. Akamatsu et al.

Page 1 of 1

It is certified that error appears in the above-identified patent and that said Letters Patent is hereby corrected as shown below:

Column 1,
Line 7, "modem" is changed to -- modern --.
Lines 51 and 53, "the factor" is deleted.

Column 3,
Line 36, "or" is deleted.

Column 6,
Line 37, -- , -- is inserted between "position" and "or".
Line 56, "-data" is deleted, and -- data -- is inserted.

Column 7,
Line 32, "of" is changed to -- a --.

Column 8,
Line 22, "rotation" is deleted.
Line 26, after "variation" -- in the -- is inserted.

Column 9,
Line 6, "a" is deleted.
Line 7, after "of" -- a -- is inserted.

Signed and Sealed this

Nineteenth Day of October, 2004

JON W. DUDAS
*Director of the United States Patent and Trademark Office*